(12) United States Patent
Brem et al.

(10) Patent No.: US 7,351,876 B2
(45) Date of Patent: Apr. 1, 2008

(54) EFFICIENT NUCLEAR TRANSFER WITH PRIMORDIAL GAMETES

(75) Inventors: Gottfried Brem, Hilgertshause (DE); Gabriela Durcova-Hills, Oberschleiβheim (DE); Sigrid Müller, Vienna (AT); Wolfgang Schernthaner, Oberscheliβheim (DE); Hendrik Wenigerkind, Vienna (AT); Eckhard Wolf, Vienna (AT); Valeri Zakhartchenko, Oberschleiβheim (DE)

(73) Assignee: Agrobiogen GmbH Biotechnologie, Hilgertshausen (DE)

( * ) Notice: Subject to any disclaimer, the term of this patent is extended or adjusted under 35 U.S.C. 154(b) by 536 days.

(21) Appl. No.: 10/242,275

(22) Filed: Sep. 12, 2002

(65) Prior Publication Data

US 2003/0051265 A1    Mar. 13, 2003

Related U.S. Application Data

(63) Continuation of application No. 09/600,547, filed as application No. PCT/EP98/00229 on Jan. 16, 1998, now abandoned.

(51) Int. Cl.
*C12N 15/00* (2006.01)
*A01K 67/027* (2006.01)

(52) U.S. Cl. .......................... 800/24; 800/15
(58) Field of Classification Search ................ 435/455, 435/463, 320.1, 325; 800/18, 21, 22, 3, 25, 800/15, 24
See application file for complete search history.

(56) References Cited

U.S. PATENT DOCUMENTS 6,271,436 B1 *  8/2001  Piedrahita et al. ............. 800/21

FOREIGN PATENT DOCUMENTS

| | | |
|---|---|---|
| EP | 0 451 823 A | 10/1991 |
| EP | 0 774 510 A | 5/1997 |
| WO | WO 95 10599 A | 4/1995 |
| WO | WO 97 07668 A | 3/1997 |
| WO | WO 97 25412 A | 7/1997 |

OTHER PUBLICATIONS

Weiss. Histology: Cell and Tissue Biology, 5th Ed. Elsevier, 1983, pp. 1020-1021.*
Oback et al. Cloning & Stem Cells, 4(2):147-168 (2002).*
Fulka et al. BioEssays, 20:847-851 (1998).*
Kono. J. of Reprod. Fertil., 2:74-80 (1997).*
Wolf et al. J. of Biotech., 65:99-110 (1998).*
Clark et al. Transgenic Research, 9:263-275 (2000).*
Dennig et al. Cloning and Stem Cells, 3(4): 221-231 (2001).*
Lavoir et al. Bio of Reprod, vol. 56, Jan. 1997, pp. 194-199.*
Liu et al. Int. Dev. Bio., 39:639-644 (1995).*
Vogel. Science, 300:225 and 227 (2003).*
Simerly et al. Dev. Bio., 276:237-252 (2004).*
Schnieke et al. Science, 278: 2130-2133 (Dec. 19, 1997).*
Bowen et al. Biol. of Reprod. 50:664-668 (1994).*
Encyclœdia Britannica online, term "culture"; http://www.search.eb.com/dictionary?hdwd=culture&book=Dictionary&jump=culture%5B2%2Ctransitive+verb%5D&list=culture%5B1%2Cnoun%5D%3D247197%3Bculture%5B2%2Ctransitive+verb%5D%3D2472152%3Bculture+shock%3D247252%3Btissue+culture%3D1138433, accessed online, Oct. 29, 2006.*
Shim et al. Biol. of Reprod., 57:1089-1095, 1997.*
Choi et al. Animal Reprod. Science, 52:17-25, 1998.*
Zakhartchenko et al. Mol. Reprod. And Dev., 52-421-426, 1999.*
Delhaise F. et al., *Nuclear Transplantation Using Bovine Primordial Germ Cells From Male Fetuses*, Reproduction Fertility and Development, Bd. 7, Nr. 5, 1995, Seiten 1217-1219.
Brem G et al., *Mammary Gland Specific Expression of Chymosin Constructs in Transgenic Rabbits*, Theriogenology, Bd. 43, Nr. 1, Jan. 1995, Seite 175.

* cited by examiner

*Primary Examiner*—Thaian N. Ton
(74) *Attorney, Agent, or Firm*—Kinney & Lange, PA

(57) ABSTRACT

This invention relates to a method for breeding animals via cloning and the animals obtainable by the method, in particular a method for reproducing animal embryos via efficient nuclear transfer with primordial gametes.

4 Claims, No Drawings

EFFICIENT NUCLEAR TRANSFER WITH PRIMORDIAL GAMETES

The present invention relates to a method for breeding animals through cloning and the animals obtainable by the method. This invention relates in particular to a method for cloning animals through efficient nuclear transfer with specific foetal cells.

Animals, in particular economically useful animals, have long been bred and further developed with respect to specific properties by man for a very wide range of purposes. Thus, for example, cows and bulls with a high breeding value for milk output have been mated to obtain animals with a high milk yield.

In recent years, animals, in particular members of the ungulates, such as sheep, cattle or cows, have become the focal point of research as producers of substances of importance in terms of nutrition or pharmaceuticals, since the development of genetic engineering has made it possible specifically to produce animals to which it is possible to impart a novel property, for example the ability to produce a specific drug. However, the problem with the commercial use of such animals is that the genetic construct transferred to them is passed on to the progeny in an integrated and stable manner.

For this purpose, attempts were made to solve the problem of gene transfer by performing it in cells, animals being generated again from these cells by means of cloning.

Among those skilled in the art, the term "cloning" is generally defined as replication of genetic material, derived from a single cell, which, when applied to embryology, may be understood as meaning the creation of embryos or animals of identical genotype. In embryology, the germ during blastogenesis, i.e. up to the development of primordial organs, is referred to as an embryo, and in the subsequent development stages as a foetus. Depending on species, embryonic phases have periods of different lengths, for example a period of about 4 weeks in cattle, and shorter or longer periods may be necessary for this purpose in other species within the ungulates.

To date, several routes have been taken for the cloning of animals, i.e. for the replication of a genotype peculiar to a specific animal.

On the one hand, early embryonic stages and further developments were subjected to microsurgery and the parts isolated therefrom in each case were grown on in vitro or in vivo.

Furthermore, a micromanipulatory combination of asynchronous development stages, referred to as "chimeral clones" was performed, in which blastomer(s) from embryos of more advanced stages were combined with blastomers from earlier stages with the aim of supporting the first-mentioned in their further development capacity and thus producing identical multiple individuals. However, the largest number of clones obtained thereby was only of the order of magnitude of not more than 5-8.

A further procedure was the parthenogenic activation or the mating of homozygous parent animals in order to obtain clones having specific properties.

Since, however, the above-mentioned method proved relatively poor in terms of their effectiveness and reliability, a further method was developed, which is generally referred to as nuclear transfer.

Here, cell nuclei which originate from multicellular embryos are transferred to appropriately prepared ova, it being possible to create genetically identical embryos.

To be able to carry out cloning successfully by means of nuclear transfer, however, some essential parameters must be taken into account.

The ovum used as the recipient cell must have completed the metaphase stage in the 2nd meiotic division (metaphase II) and should no longer contain any of its own nuclear DNA, i.e. it should be present as a so-called enucleated ovum. Furthermore, the cytoplasm of the ovum should be influenced as little as possible, since the substances contained in the cytoplasm itself may be important for the further development, for example the division of the cell.

Moreover, the nuclear DNA of the transferred nucleus must be reprogrammed. Since the "donor" nucleus originates from a multicellular embryo, the respective donor cell has already passed through some division cycles. This means that the cell is in a stage of development which is advanced in comparison with a totipotent fertilized ovum and in which specific genes required for the early development may already have been switched off.

For this reason, the nuclear DNA used must be reprogrammed in such a way that the complete genetic information of the nuclear DNA is available again and the division process of the embryo begins again in the zygote stage. Thus, the better this reprogramming or activation can be achieved, the higher is the probability of successful cloning, with which a fully developed, i.e. live-born cloned animal can subsequently also be obtained.

In addition to the nuclear DNA, inter alia, the mRNA present in the cytoplasm is also important since, at the instant of union of ovum and donor cell, said mRNA contains the messengers required for the present development or differentiation stage of the donor cell and the proteins produced therewith can influence the further development of the cell.

The method of nuclear transfer has already been used with modest success. Thus, Willadsen et al. (Nature 320 (1986), 63-65) report on the cloning of lambs, the nuclei originating from nucleus donor cells from the 8-cell stage. Robl et al. (J. Anim. Sci. 64 (1987), 642-647) reported on the first nuclear transfer experiment in cattle, exclusively cattle embryos obtained ex vivo being used as nucleus donors. In these experiments, an in vivo intermediate culture in sheep's oviducts was always required. In the following years it was also possible to show that embryonic cloning in cattle can be carried out successfully in vitro, i.e. using embryos produced in vitro and ova matured in vitro (Sims et al., Proc. Natl. Acad. Sci. USA 91 (1991), 6143-6147).

WO 97/07668 furthermore describes a method for reproducing an animal embryo, in which in general a nucleus having a diploid chromosome set is transferred to an enucleated ovum which is kept in the metaphase stage II, a certain time being allowed to elapse before the ovum is activated after introduction of the nucleus. As a result of the later activation of the ovum after introduction of the nuclear DNA, it is intended to achieve improved reprogramming of the nuclear DNA introduced.

WO 96/07732 likewise describes a method for reproducing an animal embryo, in which cells from the blastoderm of an embryo are isolated in the blastocyst stage and allowed to mature in a suitable environment and their nuclei are then introduced into suitable cells.

However, a remaining problem with this technology is that of finding for the nuclear transfer suitable donor cells with which it is possible to produce an animal embryo most expediently and economically. It is known that the reprogramming of the nuclear DNA from the donor cell chosen in each case gives rise to the greatest difficulty in embryo cloning, since this influences not only the further early maturing of the embryo but also the later development after any implantation into a mother animal. Thus, in spite of all successes in this area, there are still problems with regard to effective reprogramming of the donor nuclear DNA in order to ensure that the manipulated ovum with the new nucleus approaches the state of a natural zygote. This was manifested inter alia in an extremely low yield with respect to the production of embryonic blastocysts and a low rate of division.

It is therefore the object of the present invention to overcome the disadvantages of the prior art and to provide a suitable nucleus donor cell with which an improved method for cloning animals can be provided.

This object is achieved by a method for cloning an animal embryo, in which primordial gametes are used as the donor cell for the nuclear transfer. The nucleus of this cell is combined with a suitable recipient cell, and the cell thus obtained is grown for a period so that a blastocyst forms. The blastocysts obtainable therefrom can, if required, then be introduced into a mother animal for carrying to full term.

According to a preferred embodiment of the present invention, the recipient cell is an enucleated ovum, into which the nucleus of the primordial gamete can be introduced for nuclear transfer or with which the primordial gamete itself is fused. The primordial gamete can be obtained from a foetus and used directly or after long culture.

The animals for which the method according to the invention can be carried out are, for example, ungulates, rabbits, rodents or birds, ungulates, in particular pigs, sheep, goats, cattle or cows, being preferred.

In a preferred embodiment, the primordial gametes used in the method are transgenic, i.e. they contain one or more genes which are derived either from an exogenous source or which constitute an endogenous gene introduced at another normatural locus in the genome. These genes preferably code for a drug, for example an antibody, or a nutritionally interesting substance, for example chymosin or trypsin, it being possible for the gene in each case to be under the control of an or of the endogenous or of an exogenous promoter.

To obtain primordial gametes, foetuses are obtained from pregnant animals, and the cells are obtained, for example, by abstraction from the foetus. The desired primordial gametes are then selected from the cells obtained from the foetus, for example by allowing existing fibroblasts to adhere to the culture vessel, allowing the gametes to grow on suitable feeder cells or mechanical selection by means of a pipette. Owing to their phenotype, primordial gametes can be distinguished from other cells since they can be identified as irregularly shaped or round cells which have a slightly yellowish appearance and a large nucleus and may exhibit "blebbing" phenomena. Thus, the desired primordial cells can then be isolated.

For the following steps, the primordial gametes obtained can be used as such, or the nucleus can be isolated therefrom and further used.

As a rule, enucleated ova which are matured in vivo or in vitro are used as recipient cells. Thus, for example, unfertilized ova which were matured in vitro and from which the surrounding cumulus cells were removed after reaching metaphase II can be used.

The recipient cell should preferably have no nuclear DNA of its own. Several possibilities are available in the prior art for removing the DNA of the ovum, for example the division of the ovum into two halves, of which one half no longer has any nucleus and can be further used, or exposure to ultraviolet light for destroying the endogenous cell DNA. Removal of the nucleus or of the pronuclei or of the metaphase plate by means of micromanipulation is also possible. A treatment of the ova prior to the micromanipulation with cytochalasin B with subsequent extraction of the cytoplasm present in the vicinity of the polar body with the aid of a pipette, for example guided by a Leitz micromanipulator (Leica, Bensheim, Germany), has proved preferable. Since the nuclear DNA of the ovum is at this time localized in the vicinity of the polar bodies, the enucleation rate in this method is very high, at the same time only a small part of the cytoplasm being abstracted.

After the cells involved in each case in the nuclear transfer have been obtained, in general two routes can be taken. The nucleus of the primordial gametes is isolated using established methods known from the prior art and is introduced into the prepared recipient cell, for example by means of injection, or the primordial gamete itself is fused with the recipient cell.

In the case of a fusion, a primordial gamete can be pushed with the aid of a suitable apparatus, such as a transfer pipette, under the zona pellucida of the enucleated cell and deposited there. For integration of the nucleus of the primordial gamete into the cell plasma of the ovum, the membrane of the fibroblast is fused with the membrane of the ovum. The techniques for the fusion of cells are well known in the prior art, for example fusion using the Sendai virus, treatment with PEG (polyethylene glycol), laser fusion or electroshock. The last-mentioned method, so-called electrofusion, in which pores which permit fusion of the cytoplasm are induced by brief direct current pulses of about 1 to 5 kV/cm, preferably 1 to 3 kV/cm, with a respective duration of 2 μsec to 1 sec, which may be repeated, for example 2 to 10 times, is preferred in the present method since, if they are of suitable strength, the electric pulses can simultaneously result in activation of the (fused) ovum. The activation can also be effected a few hours (about 2-5 hours) after the fusion, for example by incubation of the fused cell in a 7% alcohol solution, preferably a 7% ethanol solution, or by means of other methods known in the prior art.

Activation of the fused cell is an important step since it is the prerequisite for initiation of the dividing activity of the fusion product. After fusion and activation are complete, the gamete-ovum complexes (nuclear transfer embryos) are cultured until they reach a stage in which they can, if required, be transferred to a recipient. If desired, substances which support or inhibit the aggregation of microtubuli can be added to the culture medium used. Nocadazol and colcemid are examples of aggregation-inhibiting agents, and taxol is a microtubuli stabilizer. These substances prevent any formation of a plurality of pronuclei.

In the existing methods of the prior art, for further culture of the embryos forming, it was necessary to transfer them carefully to an intermediate recipient. This was achieved in general by transferring the embryo, packed in a protective medium, such as agar, to the oviducts of an "interim mother animal" (temporary recipient), in which a further development until implantation in the (final) mother animal was required. In the method according to the invention, however, it is also possible to use existing in vitro systems for the cultivation, without adversely affecting the yields. Without being tied to any theory, this fact might be associated with a choice of the donor cell with which it is possible to obtain embryos which very closely approach naturally produced embryos with respect to their development. The cells are cultured for a period until blastocysts form. This comprises a period of up to 10 days, preferably 6 to 7 days.

According to the invention, it is now possible to allow cloned embryos to grow into foetuses, which might then be used again as nucleus donors. In this so-called recloning, the number of cloned embryos can be further increased.

The primordial gametes for use in the method according to the invention can be obtained from a multiplicity of animals, such as, for example, from mammals, ungulates, rabbits, rodents, such as, for example, rats or mice, or birds, such as, for example, ducks, geese or chickens. Inter alia from economic points of view, ungulates are preferred, such as, for example, cattle, sheep, goats, buffalo, camels and pigs. Sheep or cows are most preferred.

To facilitate the isolation of the gene product, the gene product can be directed to a product of the animal itself, for example to the milk in the case of cows or sheep or to the eggs in the case of birds. This can be achieved by the choice of suitable promoters for organ-specific expression, which are known from the prior art. However, the gene product can also be obtained from the animal itself, for example from the serum. It is also possible for the organ(s)/tissues of the animals to constitute the desired product, for example for (xeno) transplantation.

The primordial gametes used in the method according to the invention or the foetuses or animals from which they are derived can moreover be transgenic, the transgene preferably coding for a nutritionally or pharmaceutically interesting product, for example an antibody. For example, in cows or sheep, the gene for chymosin or trypsin can be incorporated in a construct which permits the production of the corresponding enzyme or of one of its precursors in the animal's milk. The transgene of interest can, depending on requirements, be under the control of an exogenous, likewise transgenic promoter, or a known endogenous promoter can be used for this purpose.

By means of the method according to the invention, it is now possible to achieve an improvement in the production of homologous animal proteins, a modification of animal products, such as milk itself, or the production of animal organs for, for example, medical use.

A large number of proteins have been produced to date from animal organs by purification from these organs and then used in medicine or technology. Problems exist, inter alia, with regard to the relative amounts in which they are present in these tissues (for example FSH from pituitary glands), which leads to high production costs since on the one hand a large amount of starting material, i.e. many animals, are required for production, which, owing to the large number of animals, entails the danger of contamination with, for example, pathogens such as BSE or Ehec.

Examples of interesting proteins obtained from animal organs are aprotinin from the lung, chymosin from the stomach, catalase from the liver, elastase, pancreatin, insulin or trypsin from the pancreas, hyaluronidase from testicles, chrondroitin from the trachea, collagens from the skin, fibronectin or vitronectin from plasma, epithelial cell growth suppl. or LH (luteinising hormone) from the pituitary gland, fibroblast growth factor or gangliosides from the brain, and haemoglobin, thrombin, transferrin, etc. This list should not be regarded as imposing any restrictions.

For all these products, an ectotopic expression, i.e. an expression in another tissue, for example in the mammary gland, can be achieved if an additive gene transfer was carried out beforehand, for example via injection, transformation, transfection or by another method known from the prior art, in the cells used for cloning, a gene construct recombined in vitro additionally being integrated into the genome. In addition, by homologous recombination in the cells, it is possible to ensure the gene present endogenously is coupled with a promoter which gives another expression pattern for this structural gene, for example production of chymosin in the udder with associated secretion in the milk instead of endogenous synthesis in the stomach. Furthermore, a promoter present endogenously, for example the casein or lactoglobulin promoter can be coupled with a new structural gene so that optimum conditions are present for the expression. In both above-mentioned cases, promoter and structural gene, which are recombined into the genome are isolated beforehand from a gene bank which has been obtained, for example, from primordial gametes, so that the DNA used is not only endogenous to the species (self-cloning) but also isogenous DNA.

In this way, the composition of foods obtained from animal products, such as, for example, milk, can be altered in the desired manner so that they have positive alimentary, dietary, health-promoting properties or a lower allergenic potential or better shelf-life or processing properties. Thus, for example, milk containing Ehec antibodies or milk having properties specially tailored to diseases, such as, for example, lactose intolerance, can be produced.

In addition, by using MACs (mammalian artificial chromosomes), integrational mutations can be avoided and large DNA fragments transferred. These MACs are replicated as additional mini- or microchromosomes in the nucleus in exactly the same way as the endogenous chromosomes. Thus, it is possible, for example, to transfer gene clusters beyond the species, for example complete human immunoglobulin gene clusters to economically useful animals, and these economically useful animals would then be capable of producing human antibodies, which could be recovered and used. The transfer of specific MACs from the same species furthermore means that, with cumulative genetic effects, there would be an increase in the synthesis of the gene product.

Also important is an expression of homologous proteins or of possibly transgenic tissues or organs in economically useful animals, in the case of proteins in the same organs in which these proteins are also expressed in humans. The proteins are then obtained by methods known in the prior art, and the tissues or organs are removed from the animal before eventual transplantation. The advantage of this procedure is a high identity of the expressed proteins since they are processed or post-translationally modified in the correct organ, for example the expression of erythropoietin in the kidney. The result of this is that the proteins obtained from the different tissues have the same glycosylation as the substances in humans themselves, their activity very closely approaching that of the natural protein. It is thus possible to obtain transgenic animals, for example pigs, cattle, etc., which produce human insulin, erythropoietin, etc., which can then be better used in medicine.

On the basis of the method according to the invention, an economically useful animal produced transgenically and having, for example, the above-mentioned properties can then be propagated in a stable manner.

Thus, efficient production of relatively large clone groups of transgenic animals can be achieved by the following procedure, as shown schematically below:

1. Micromanipulation of Zygotes

A prepared gene construct (for example as described in German Offenlegungsschrift 40 12 526) is introduced into a fertilized ovum and integrates into the genome. This is a normal gene transfer with cumulative, random integration of the gene construct into the genome of the zygote. It is also possible to carry out a homologous recombination in which simultaneously an endogenous gene can be eliminated or an endogenous promoter/an endogenous gene can be used.

2. In vitro Culture

The zygote is cultivated in a suitable medium briefly, i.e. for 1-5 hours or for several days, for example 1 to 8 days. It can also be transferred immediately into the oviduct of a suitable recipient animal.

3. Transfer to Recipient

The zygote is transferred into the oviduct or the uterus of a recipient animal for further development into an embryo, it being possible to transfer up to 4 embryos.

4. Isolation of the Embryo or Foetus

The foetus is isolated, for example by sacrificing the recipient animal and removing the foetus. Other methods of isolating the embryo without sacrificing the recipient animal are also possible.

5. Selection for Transgenic Foetuses

Cells of the embryo are isolated and are investigated with respect to integration of the gene construct.

6. Isolation of Primordial Gametes From the Foetuses

The primordial gametes from foetuses which have integrated the gene construct are isolated and further used.

7. Cloning

The nuclei of transgenic, primordial gametes are combined with suitable recipient cells (nucleus transfer, fusion) and treated as explained in more detail here.

8. In vitro Culture

The cells are cultured in vitro for a period of about 4 to 10 days.

9. Transfer to Recipient

The cell clusters (blastocysts) forming are again transferred to recipient animals. Before the transfer, the zona pellucida is slit, which has proved particularly suitable.

10. Repetition of the Method from 6. to 9.

The present invention also relates to the cloned animals which are obtainable by the method according to the invention and which, as explained above, may or may not be transgenic.

Another advantage of the method according to the invention, in addition to increased efficiency, i.e. a higher success rate compared with the methods of the prior art, in the reproduction of genetically identical embryos, is that larger clone groups are obtainable. Thus, an already cloned foetus can be used for producing further clones, since the foetal cells can be recovered and efficiently reused in vitro (point 10 of the above-mentioned method).

Thus, using the method according to the invention, it was possible to obtain results which were even better than those obtained from punctured oocytes with subsequent maturation and fertilization—but without cloning. The higher in vivo development capacity observed considerably increases the efficiency of the cloning programmes.

The so-called gravidity rate (gestation rate) can serve as a measure of the efficiency of such methods and can be determined as the proportion of animals which have become pregnant after transfer of embryos cultivated in vitro for 6-7 days to synchronized recipient animals. The respective gravidity rates can be determined by measurement of the progesterone level, ultrasonic investigations or rectal palpation.

For cattle as an example, the following results were obtained by different methods:

| Gravidity rates: | |
|---|---|
| Ooctye puncture with subsequent IVM and IVF | 34% |
| Embryo cloning (average) | 25% |
| Embryo cloning with primordial gametes | >50% |

IVM = in vitro maturation
IVF = in vitro fertilization

The invention is now explained in detail with reference to the example which is given merely for illustration and is not intended to restrict the scope of the invention.

EXAMPLE

Isolation of Primordial Gametes in the Bovine Foetus

Foetuses from uteri of sacrificed female calves or cows were isolated and placed in PBS (phosphate buffered saline, without $Ca^{2+}/Mg^{2+}$, with penicillin/streptomycin, plus 10% of foetal calfs serum (FCS)) on ice water in the laboratory. The foetuses were then washed several times with fresh PBS. Each foetus was divided transversely, caudally with respect to the anterior limbs, followed by medial opening of the abdominal wall and cranial displacement of liver and intestinal convolution. Thereafter, the now exposed mesonephros and the median gonads were isolated and were washed in fresh PBS. The gonads were removed by means of forceps and again washed in PBS. They were then incubated in 0.02% EDTA for 10 to 20 minutes. Incubation in 0.4% protease (Sigma, P 6911) for 3-8 minutes at 37-39° C. achieved the same effect.

The gonad cells were transferred by means of a pipette to culture medium containing added growth factors (Dulbecco's modified Eagle Medium (Gibco), supplemented with 15% of FCS, 2 mM L-glutamine, $10^{-7}$ mmol β-mercaptoethanol, 2 mmol nonessential amino acids, LIF (Leukemia Inhibitory Factor, 1000 units/ml), bFGF (basic Fibroblast Growth Factor, 10 ng/ml) and penicillin/streptomycin), a cell culture being obtained. Alternatively, the gonads were punctured several times with a 30 G needle (gauge) and the cells taken up and released by means of a pipette until a cell suspension was present. The cells were then carefully separated off by centrifuging in a tabletop centrifuge at 1100 rpm (160 g) for 4 minutes and then resuspended in culture medium.

The resuspended cells were then cultured in 35 mm Petri dishes at 37 to 39° C. with 5% of $CO_2$ in water vapour-saturated air until required for use.

For isolation of the cells for cloning, the cell suspension was transferred to a 4 cm cell culture dish and kept for 20-22 hours in Dulbecco's modified Eagle Medium (Gibco) (supra) at 37-39° C. with 5% of $CO_2$. 15 minutes prior to the beginning of cloning, the cells were treated briefly (1-2 minutes) with a 0.1% trypsin solution (Sigma) to bring them completely into suspension.

For further selection with respect to primordial gametes and their proliferation, the culture (containing gametes, fibroblasts, erythrocytes, etc.) was then transferred to feeder cells. Bovine fibroblasts, untransfected STO cells (ATCC CRL-1503) or deactivated primordial gonads were successfully used as feeder cells. The culture medium was DMEM (Gibco, No. 074-2100A) (high glucose), which had been supplemented with 15% FCS, 2 mmol nonessential amino acids, 2 mmol L-glutamine, $10^{-4}$ β-mercaptoethanol, penicillin/streptomycin, 1000 IU/ml LIF and 10 ng/ml bFGF.

Alternatively, the primordial gametes were transferred selectively from the cell culture using a pipette to a new dish, with the result that the number of "foreign" cells could be minimized.

The primordial gametes which are to be used as nucleus donors can be identified in the cell suspension as large (15-25 μm), irregularly shaped or round cells which have a yellowish appearance and a large nucleus and sometimes exhibit "blebbing" phenomena. These cells could be selectively isolated.

Additive Gene Transfer

Gene constructs recombined in vitro, as described in German Offenlegungsschrift 40 12 526, which is hereby incorporated by reference, are integrated in a stable manner by conventional DNA microinjection (Brem G., Transgenic Animals, Genetic Engineering of Animals, VCH Weinheim (1993), 83-170) into the nuclei of isolated primordial gametes or by known transformation methods (Maniatis et al., Molecular Cloning, A Laboratory Manual, Cold Spring Harbor Laboratory, 1989). The detection of the integration into the cells is performed by means of PCR and/or Southern Blotting (Maniatis, above). An expression in well differentiated cells shows that the gene transfer has been successful.

Cloning 18-20 hours after the beginning of maturation, bovine oocytes isolated from the ovary were freed from the cumulus cells surrounding them and were enucleated within two hours (Molecular Reproduction and Development 42 (1995), 53-57). About 20-22 hours after the beginning of maturation, primordial gametes isolated as above were transferred by means of a transfer pipette into the perivitelline space of enucleated oocytes and the resulting karioplast-cytoplast complexes (KCC) were each exposed to a double electrical pulse of 2.1 kV/cm for 10 μsec in order to induce fusion. The KCCs were cultivated in Ham's F-12 Medium (Sigma) with 10% FCS in an incubator. The fusion was assessed 30 to 60 minutes after the fusion pulse, by microscopic investigation.

24 hours after the beginning of maturation, the KCCs were activated by incubation for 5 minutes in 7% ethanol and then cultivated for 5 hours in 10 μg/ml cyclohexamide (Sigma C-7698) and 5 μg/ml cytochalasin B (Sigma, C-6762). The KCCs were then transferred in a 100 μl drop of CR-1 Medium (Rosenkrans and First, 1991) with 10% of oestrus cow serum. The drops were covered with a layer of liquid paraffin and cultivated for 7 to 8 days at 39° C. in water vapour-saturated atmosphere comprising 5% of $CO_2$, 5% of $O_2$ and 90% of $N_2$.

TABLE

| | Primordial gametes (PG) as nucleus donors | | | |
|---|---|---|---|---|
| | KCC | Fused KCC (%) | Division (%) | Blastocysts (%) |
| PG foetus 50-57 days | 139 | 109 (74%) | 77 (71%) | 38 (35%) |
| PG foetus 65-76 days | 143 | 128 (90%) | 81 (63%) | 32 (25%) |
| PG foetus 95-105 days | 171 | 171 (87%) | 90 (60%) | 30 (20%) |

TABLE-continued

| | Primordial gametes (PG) as nucleus donors | | | |
|---|---|---|---|---|
| | KCC | Fused KCC (%) | Division (%) | Blastocysts (%) |
| Embryonic blastomers | 111 | 108 (97%) | 66 (61%) | 3 (3%) |

As is evident from the above Table, it was possible as early as the first experiment to obtain a rate of division of up to 71% and a blastocyst rate of up to 35%.

Embryo Transfer

Management of Recipients

The recipients used were female calves which fulfilled the following criteria:

1. Bred in farms where no IBR (bovine Herpes virus Type 1) was suspected;
2. serological investigation for BHV-1 antibodies (infectious bovine rhinotracheitis/infectious pustular vulvovaginitis) negative;
3. serological investigation for BVD (bovine virus diarrhoea)/MD antigen (mucosal disease) negative;
4. body mass development corresponding to the age (13-16 months);
5. sexual maturity reached; in animals which are to carry the embryo to term, breeding maturity reached;
6. gynaecological examination without pathological results.

Immediately after stabling, all recipients received mineral boli (All Trace, Ranching Consult GmbH) in order to supplement the selenium, copper and cobalt supplied, which experience has shown to be insufficient (Wittkowsi et al., Zur Selensupplementierung bei Färsen [Supplementation in heifers]; Jahrestagung der Arbeitsgemeinschaft Embryotransfer Deutschland (AET-d), 13.06.-14.06.1996, Marktredwitz).

BVD antibody-negative animals were immunized against BVD/MD (Rumilis®, Intervet) in order to minimize the risk of infection on transfer of embryos (Mödl et al., Control of bovine viral diarrhea virus in abbatoir ovaries for in vitro fertilization (IVF) or cloning programs. 11e Reunion A.E.T.E. Hanover, 8-9 Sep. 1995) or after placing in stables with unknown BVD status. The animals were fed ad libitum with grass silage, hay and straw. Deworming was performed in the spring and autumn with ivermectin (Ivornec®, MSD Agvet). Some of the recipients were housed in covered cattle yards (open-sided cattle sheds, group size 6 animals) and some in rearing housing.

Preparation of Recipients

The embryos prepared in vitro were transferred to recipients with synchronized menstruation, i.e. the stage of the sexual cycle corresponds to the age of the embryo to be transferred. The day of oestrus is regarded as day 0 of the cycle. The oestrus synchronization was carried out in the dioestrus by a single intramuscular administration of a prostaglandin $F_2$-α-analogue (2.0 ml of Estrumate® Mallinckrodt Veterinary). Female calves in which no functional corpus luteum was diagnosable by means of rectal palpation were not used for the oestrus synchronization. Experience shows that oestrus occurs 2-3 days after administration and is assessed on the basis of the oestrus behaviour and of the finding in the vaginal examination.

Embryo Transfer

The embryos produced in vitro were transferred after culture for 7 days to suitable recipients. For this purpose, the embryos were identified and qualitatively assessed, the zona was slit and said embryos were transferred to a suitable transfer medium and then drawn into minipaillettes (Minitüb). The transfer media used were PBS+10% of foetal calf's serum (FCS, Biochrom), Ovum Culture Medium (ICP, New Zealand)+10% of FCS or TL-Hepes+10% of FCS.

The closed paillettes were stored at 37.8° C. in a miniincubator until the transfer, which was to take place within about 90 minutes.

The suitability of the recipients was assessed on the basis of the following criteria:

The animals were observed in oestrus about 7 days before transfer, and the asynchronism should not exceed 24 hours (Hasler et al., Theriogenology 43 (1995), 141-152). The presence and the size of a functional corpus luteum were evaluated accordingly (Assey et al., Theriogenology 39 (1993), 1321-1330).

The animals used showed no signs of disease of the genital tract.

After the selection, an epidural anaesthetic (2.0 ml of Lidocain®, Albrecht) was given and the external genital organ was carefully cleaned with dry paper. Thereafter, the transfer catheter (Minitüb) at body heat was loaded with a paillette and provided with a plastic protective sheath (Sanisheath, Minitüb). The transfer was performed bloodlessly with rectal monitoring of the cervical passage and of the catheter position into the apex of the ipsilateral uterine cornu (Reichenbach et al., J. Reprod. Fertil. 95 (1992), 363-370). The plastic protective sheath was perforated with the transfer catheter only at the external os uteri, in order to avoid entrainment of germs from the vagina into the uterus. If it was intended to transfer a plurality of embryos to one recipient, these were transferred bilaterally. For this purpose, the transfer catheter was drawn back into the body of the uterus, the guide with the emptied paillette was removed, a new paillette containing embryo(s) was pushed into the catheter and the latter was positioned in the contralateral uterine cornu. Immediately after the transfer, all relevant data (vital number of the recipient, origin, number and quality of the embryos, etc.) were documented.

Gestation Examination 21 days after oestrus, i.e. 14 days after the embryo transfer, an oestrus check was performed and the progesterone content of the blood serum was determined. Values of less than 0.1 ng/ml are regarded with certainty as indicating the absence of gestation. At progesterone values of more than 2.0 ng/ml, gestation can be expected. The first direct gestation examination was carried out on about the 35th day by means of ultrasonics and the second was carried out manually on about the 42nd day of gestation.

The invention claimed is:

1. A method of producing a bovine blastocyst, the method comprising the steps of:
    (a) isolating a bovine primordial gamete from a bovine foetus by mechanically selecting the bovine primordial gamete from cells obtained from the bovine foetus;
    (b) combining directly the nucleus of the bovine primordial gamete with an enucleated bovine oocyte to form a cell;
    (c) activating the cell obtained in step (b); and
    (d) cultivating the cell in an in vitro system for a time that is sufficient to form the bovine blastocyst.

2. The method of claim 1 wherein the bovine primordial gamete is fused with the enucleated bovine oocyte.

3. The method of claim 1 wherein the bovine primordial gamete is derived from a transgenic bovine and includes at least one transgene that is under the control of an exogenous promoter or an endogenous promoter.

4. The method of claim 3 wherein the transgene encodes for a pharmaceutical product, a nutritional product, or any combination of any of these.

* * * * *